United States Patent [19]

Ölund et al.

[11] Patent Number: 5,550,145
[45] Date of Patent: Aug. 27, 1996

[54] POTENTIATION OF ANTIMICROBIAL EFFECTS

[75] Inventors: Karin Ölund, Kollegievägen; Lena-Karin Lütz, Ronnebygatan; Rickard Bryland, Rönneholmsvägen; Åke Lindahl, Ringduvevägen, all of Sweden

[73] Assignee: Bioglan AB, Malmo, Sweden

[21] Appl. No.: 307,763

[22] PCT Filed: Mar. 31, 1993

[86] PCT No.: PCT/SE93/00275

§ 371 Date: Sep. 27, 1994

§ 102(e) Date: Sep. 27, 1994

[87] PCT Pub. No.: WO93/20812

PCT Pub. Date: Oct. 28, 1993

[30] Foreign Application Priority Data

Apr. 14, 1992 [SE] Sweden ................... 9201187

[51] Int. Cl.⁶ .................. A61K 47/00; A61K 31/23
[52] U.S. Cl. ............... 514/396; 514/398; 514/399; 514/552; 514/569; 514/570; 514/577; 514/588; 514/709; 514/727; 514/738; 514/732; 514/739; 514/758; 514/765; 514/766; 514/786
[58] Field of Search .................. 514/398, 399, 514/552, 396, 588, 569, 570, 577, 709, 738, 727, 758, 732, 739, 765, 766, 786

[56] References Cited

U.S. PATENT DOCUMENTS 3,772,446  11/1973  Larsson .
4,067,997  1/1978   Cardin et al. .
4,847,088  7/1989   Blank ........................... 424/404

FOREIGN PATENT DOCUMENTS 0243145  10/1987  European Pat. Off. .
0244144  11/1987  European Pat. Off. .
0465423  1/1992   European Pat. Off. .
0483835  5/1992   European Pat. Off. .
1174672  12/1969  United Kingdom .
2193892  2/1988   United Kingdom .
WO89/06124  7/1989  WIPO .
WO90/10441  9/1990  WIPO .
WO91/12010  8/1991  WIPO .
WO91/16032  10/1991 WIPO .

OTHER PUBLICATIONS

"Food Preservative Composition", STN International, File CA, Chemical Abstracts, vol. 99, No. 19, 7 Nov. 1983, Takeda Chemical Industries, Ltd., Abstract 157083w, & JP 58111669, 2 Jul. 1983.

"Food Preservative Composition", STN International, File CA, Chemical Abstracts, vol. 92, No. 7, 18 Feb. 1980, Isao Shibasaki et al., Abstract 57080w, & JP 54034061, 24 Oct. 1979.

"Antimicrobial Agents Derived from Fatty Acids", John J. Kabara, JAOCS, vol. 61, No. 2, Feb. 1984, pp. 397–403.

*Primary Examiner*—James J. Seidleck
*Assistant Examiner*—John M. Cooney, Jr.
*Attorney, Agent, or Firm*—Burns, Doane, Swecker & Mathis, L.L.P.

[57] ABSTRACT

An antimicrobial composition comprising an antimicrobially effective amount of a combination of: A) a monoglyceride of lauric acid, a monoglyceride of monomyristic acid or a mixture of these monoglycerides, and B) at least one chemical substance selected from the following groups: i) local anesthetics of the amide type; ii) carbamide, iii) antibacterial substances in the form of steroid antibiotics, imidazole derivatives or nitroimidazole derivatives, and iv) diols with 3–6 carbon atoms, and C) optionally, a conventional physiologically acceptable carrier and/or physiologically acceptable additives. A process for the preparation of this composition by heating (A) to the transition temperature of the lipid, adding (B), and optionally (C), and cooling the mixture to form a solid lipid crystal composition. Use of the composition for the preparation of a dermatological preparation for combatting bacteria and fungi or as a preservative additive in a cosmetic product, a food product, or a medical product.

28 Claims, No Drawings 5,550,145

POTENTIATION OF ANTIMICROBIAL EFFECTS

TECHNICAL FIELD

The present invention relates to a novel antimicrobial composition and to a process for the preparation thereof. The invention further relates to the composition for use as a pharmaceutical composition, to the use of the composition for the preparation of a pharmaceutical preparation as well as to usages of said composition as a preservative additive in cosmetic, medical or food products. More specifically, the composition contains certain special monoglycerides which potentiate the antimicrobial properties of previously known antimicrobial compounds or impart antimicrobial properties to compounds which have not in themselves been regarded as antimicrobials.

BACKGROUND TO THE INVENTION

The use of antibacterial substances is common within, by way of example, the field of dermatology. The aim of this use is partly to treat the patient with a specific antibacterial substance against some infection, e.g. antimycotics against fungal infections, partly to preserve the products against microbial contamination.

In cases where a patient is to be treated, specific-action antimicrobial substances without general effects are often used. The disadvantage of such treatments is that "typing", a dermination in order to enable choice of the appropriate preparation, must be undertaken before the treatment. Additionally, there is the risk that other microorganisms may invade during treatment against which the preparation has no effect.

On the other hand, if the antimicrobial substance is used as a preservative in the product, it is desirable that it has no effect on the patient, either of an antimicrobial or a toxic nature. The substances that are nowadays used for this purpose are well documented as regards preservative effects but it is also known that many of them exhibit toxic effects in some form or other.

The present invention enables the elimination or at least the drastic reduction of the above shortcomings or disadvantages.

GENERAL DESCRIPTION OF THE INVENTION

In the practice of the invention, it has surprisingly been found that the combination of particular monoglycerides with certain specific groups of chemical substances provides a synergistic effect with regard to antimicrobial properties. In this respect, it has been established that the invention not only provides a synergistic effect in relation to compounds which were previously known to exhibit certain antimicrobial properties, but that it also leads to synergistic effects in relation to chemical substances which had previously not been known to exhibit antimicrobial properties at all.

Aside from the monoglycerides used in accordance with the invention being tolerated particularly well by humans, especially due to their near relationship to substances naturally occuring in the body, many of the substances with which the monoglycerides are combined in accordance with the invention are of a type which does not give rise to any toxic effects in humans. Accordingly, the present invention opens unsuspected possibilities to produce new preparations of a medically active character as well as a preservative character and which do not give rise to any side-effects. Through The synergistic effect of the invention, it additionally becomes possible to use the "active" component in a lower concentration than previously or to use an "active" component which has previously been out of the question altogether, which can also be an advantage from a non-toxicity viewpoint. Furthermore, the new combination in accordance with the invention has proven to give rise to antimicrobial properties of a very general character and therefore even the abovementioned disadvantages with typing and very specific-action antimicrobial properties can be eliminated or reduced.

Other advantages of the invention should be apparent to the man skilled in the art after reviewing the following more detailed description of the invention.

The antimicrobial composition in accordance with the present invention is more particularly distinguished in that it comprises an antimicrobially effective amount of a combination of components A) and B), where A) is the monoglyceride of lauric acid, the monoglyceride of myristic acid or a blend of both of these monoglycerides, and component B) is at least one chemical substance selected from the following groups:

i) a local anaesthetic of the amide type;
ii) carbamide;
iii) an antimicrobial or antibacterial substance in the form of asteroid antibiotic, an imidazole derivative or a nitroimidazole derivative; and
iv) a diol with 3–6 carbon atoms.

The composition can additionally contain, if so required, C) a conventional physiologically acceptable carrier and/or physiologically acceptable additives.

The invention is thus founded on the surprising observation that the monoglyceride of lauric acid and the monoglyceride of myristic acid impart antimicrobial properties in the abovementioned groups of chemical substances where they have not previously been observed at all or potentiate the antimicrobial properties in the groups of chemical substances in question in those cases where antimicrobial properties, as such, were previously known. In this connection, it should be mentioned that John J. Kabara in the February 1984 JAOCS vol. 61:2 pp 397–403, "Antimicrobial Agents Derived from Fatty Acids", reports that the monoglycerides of, for example, lauric acid and myristic acid per se exhibit certain antimicrobial properties. However, Kabara has only demonstrated effects on Gram positive bacteria but above all else the practice of the present invention has proven that a strong synergistic effect is obtained which for example can mean that the minimum inhibitory concentration with regard to certain microorganisms is a considerable number of orders of magnitude lower than would be expected on the basis of purely accumulative effects.

Of the two monoglycerides, also known as monolaurin and monomyristin respectively, the monoglyceride of lauric acid, i.e. monolaurin, is especially preferred from an effectiveness viewpoint but also from a physiological viewpoint because for example upon application to the skin it is particularly well combinable or compatible with the lipids that are already present on the skin surface. Often, this means that monolaurin is the sole component A) in the composition or that it comprises the dominant component of the two monoglycerides, calculated by weight, but this is not necessarily always the case as the relevant monoglycerides can also function in certain preparations as carrier, vehicle or consistency agent, as will be reverted to further below.

However, for use in skin products it is particularly convenient to blend monolaurin with monomyristin because the melting point for monolaurin crystals in water is 36° C. while the blend of monolaurin and monomyristin in the proportions 1:5 to 5:1, in water, melts at 31°–32° C.

The especially preferred monoglycerides are the 1- or 3monoglycerides of lauric acid and myristic acid, respectively, e.g. 1- or 3- monolaurin and 1-monomyristin, to a not insignificant degree because the corresponding 2monoglyceride, if synthesized, is converted to the 1- or 3-monoglyceride in aqueous solution for example. In view of the above, the especially preferred monoglyceride is therefore 1-monolaurin or 3-monolaurin.

As monolaurin and monomyristin respectively are generally accepted nowadays as being completely non-toxic, it will be appreciated that additional commentary regarding the physiological acceptability of the composition of the invention need not be further elaborated here. Thus for applications in which the product comes into contact with humans those grades of the relevant monoglyceride will, of course, be selected from those which are known to be non-toxic and acceptable.

In relation to the especially preferred substances in the various B) groups, the following should be noted.

Particularly preferred local anaesthetics of the amide type, i.e. component i), are lidocaine, prilocaine, mepivacaine, cinchocaine, bupivacaine and etidocaine.

The especially preferred substance amongst said local anaesthetics is lidocaine, to a not insignificant degree due to it being well known in medical connections.

Carbamide, often also known as urea, is of interest in relation to the invention as, per se, it has been previously known and generally accepted in dermatological connections. Fusidic acid and cephalosporin P can be mentioned as preferred antimicrobial substances of the steroid antibiotic form, of which fusidic acid is especially preferred.

Econazole nitrate and miconazole nitrate can be mentioned as preferred examples of antimicrobial substances of the imidazole derivative form, of which econazole is especially preferred.

Advantageous antimicrobial substances of the nitroimidazole derivative form are tinidazole and metronidazole.

As regards the diol with 3–6 carbon atoms, i.e. component iv), propanediols, butanediols, pentanediols and hexanediols are included, of which pentanediols are preferred. The particularly preferred pentanediol is 1,5-pentanediol.

The group B) chemical substance is, of course, also selected with regard to its physiological acceptability. The latter expression should thus be interpreted broadly as the composition of the invention is usable in medical connections as well as food and cosmetic connections, as will be described further below. In other words, the expression includes "pharmaceutically acceptable" in its conventional meaning in medical connections, and similarly "acceptable" or "allowed" in food and/or cosmetic products in acordance with the regulations applying in individual countries for these types of products.

The monoglycerides A), in accordance with the invention have proven To provide usable effects even at very low concentrations and therefore the lower limit for said component can be set as low as 0.2 ppm, calculated as weight relative to the total weight of the entire composition. However, in many cases at least 1 ppm or at least 10 ppm can be required to achieve usable results in practice. On the other hand, the upper limit is virtually impossible to state in more specific figures, as the composition of the invention is often used, e.g. as a salve, cream or or lotion where the monoglyceride also functions as a carrier or consistency agent and due to this is used in concentrations of the order of several tens of percent, calculated on the total weight of the composition.

As will be apparent from the above, it is often a matter of very broad limits within which the preferred concentrations can be specified from 0.2 ppm to 30% of the total weight of the composition. Other suitable ranges within the above are from 1 ppm to 30% and from 10 ppm to 30%. However particularly preferred preparations of the salve, cream and lotion type often contain 5–30 weight percent, preferably 10–30 weight percent.

Component B) has also proven to Give the above described synergistic effect together with component A) at very low concentrations. More particularly, it can often be a matter of a lower limit of 1 ppm, 10 ppm or 100 ppm, combined with an upper limit of 20 weight percent or even better 10 weight percent. Ranges of interest within the above are from 1 ppm to 10%, from 10 ppm to 10% and from 100 ppm to 10%, respectively. However, especially with products of the salve, cream and lotion type, it can often be a matter of preferred ranges of the order 0.1–20 weight percent, in particular 0.1–10 weight percent.

As is apparent from the above, the composition of the invention is usable firstly as an active component in pharmaceutical preparations to impart antimicrobial properties to such preperations, in particular antibacterial and antifungal properties but also antiviral properties in certain cases. Secondly, as an additive, the composition of the invention acts as a preservative agent in food and cosmetic products. Additionally, they are, of course, usable in other connections where antimicrobial properties are desired, in which case the composition of the invention can be prepared in a form which is usable for the relevant application.

This means that the composition of the invention can often also contain component C), i.e. some form of physiologically acceptable carrier and/or one or more physiologically acceptable additives. Said carrier and additives are selected entirely according to conventional techniques and therfore need not be further commented upon here. However it should be stressed that the composition of the invention for use in medical connections is primarily intended for dermatological use which means that it is often prepared in the form of a salve, cream, gel, solution, lotion or emulsion to which any carrier and/or additive must be suited.

The present invention is further directed to a process for the preparation of the above defined antimicrobial composition, the above recited preferred embodiments of the composition as regards ingredients and amounts also applying in relation to the process. The process of the invention is more particularly distinguished in that: the composition is prepared in the form of a solid lipid crystal composition with surface-active hydrophilic crystals which are per se known, e.g. in GB patent publication 1,174,672.

The process in accordance with the invention for the preparation of such a lipid crystal composition includes heating the monoglyceride(s) A) to a temperature above the transition or conversion temperature of the lipid. optionally in the presence of carrier and/or additive C), adding substance(s) B) to the heated mixture and maintaining said temperature until conversion has taken place and cooling the mixture to approximately room temperature or some other desired use-temperature to produce said surface-active solid crystal composition.

A preferred embodiment of the process requires that the cooling is carried out at a rate of around 1°–3° C. per minute.

Other types of compositions in accordance with the invention are prepared by mixing components A), B) and optionally C), in per se known methods depending on the desired form of preparation.

From the above it will further be clear that a special aspect of the invention comprises the above defined composition, including all the preferred variants thereof, for use as an antimicrobial pharmaceutical composition, especially an antibacterial or antifungal pharmaceutical composition, conveniently in salve, cream, gel or lotion form or particularly in a solid crystal composition of the above mentioned type.

According to a further aspect of the invention, there is provided the use of the above mentioned composition, including the preferred embodiments thereof, for the preparation of a pharmaceutical preparation for combatting bacteria and fungi, which preparation is primarily intended for dermatological use or application to the skin.

Another use of the above mentioned composition, which also includes the preferred embodiments thereof, in accordance with the invention is as a preservative additive in various types of products which are liable to attack by bacteria or fungi, namely cosmetic, food and medical products.

DETAILED DESCRIPTION OF THE INVENTION

The invention will now be further described in relation to the following non-limiting Examples which illustrate the preparation of compositions in accordance with the invention, the constituents of these compositions, and their antimicrobial effects.

EXAMPLE 1

Antimicrobial preparation containing lidocaine

A preparation with the following composition by weight was prepared:

| | |
|---|---|
| 1-glycerol monolaurate | 5.5% |
| 1-glycerol monomyristate | 16.5% |
| Lidocaine | 5% |
| Propylene glycol | 5% |
| Purified water (Ph. Eur.) | to 100% |

Preparation was as follows: the monoglycerides were heated to 70° C. together with the water and propylene glycol, and the lidocaine added. The mixture was then cooled at a rate of 1–3° C. per minute to room temperature.

Conventional buffering substances can be added to the preparation to provide a pH of 6–7 so that the xylocaine stays in solution. Thickening agents, which can be organic or inorganic, can also be added to improve cosmetic properties, if so desired. If thickening agents are utilized, these are added to the aqueous phase prior to heating or at 70° C. Buffering substances are conveniently added at 70° C. Other substances serving to modify the properties of the product, for example in relation to taste, odour and consistency can be provided in an appropriate manner. This also applies to the remaining Examples.

The resulting preparation was tested in a Kelsey Test in which it proved to be very active against both bacteria and fungi. It was still active, from an antimicrobial viewpoint, after 6 inoculations with *Straph. aureus, Strept. faecalis, Ps. aeruginosa* and *Candida albicans*. Effects on the replication of the HSV1 and 2 viruses have been demonstrated with the above preparation.

EXAMPLE 2

Antimicrobial cream containing pentanediol

A cream with the following composition by weight was prepared:

| | |
|---|---|
| 1-glycerol monolaurate | 7% |
| 1-glycerol monomyristate | 21% |
| 1,5-pentanediol | 5% |
| Purified water | to 100% |

Additives such as consistency agents and buffering substances, for example, can be added to the product if so desired.

During preparation, the monoglcerides and water were heated to 70° C. after which the pentanediol was added. After 15 minutes agitation at said temperature, the mixture was cooled at a rate of 1°–3° C. per minute to room temperature. Addition of consistency agents or buffering substances, if any, is conveniently done prior to cooling, i.e. at 70° C. or prior to heating.

An MIC (minimum inhibitory concentration) determination showed the cream to have a 10,000 fold greater effect than a pure solution of 1,5-pentanediol on the microorganisms listed below:

| | MIC value (mg/ml) | |
|---|---|---|
| Microorganism | 1,5-pentanediol solution | Cream of the invention |
| S. aureus | 50 | 0.0013 |
| S. epidermis | 50 | 0.00075 |
| C. albicans | 40 | 0.0025 |
| T. rubrum | 10 | 0.0013 |
| P. ovale | 20 | 0.00025 |

The above MIC values clearly show that the preparation can be utilized as an antimicrobial preparation at very low concentrations.

In addition to antibacterial and antifungal effects, the preparation also has an effect on the replication of HSV1 without damage to the host cell lines, e.g. green monkey kidney cells, GMK AH 1.

EXAMPLE 3

Antimicrobial gel containing pentanediol

A preparation with the following composition by weight was prepared:

| | |
|---|---|
| 1,5 pentanediol | 5% |
| 1-glycerol monolaurate | 2% |
| Dipropylene glycol | 20% |
| Carbopol | 2% |
| NeOH | q.s. |
| Purified water | to 100% |

The 1-glycerol monolaurate was dissolved in the propylene glycol and the 1,5-pentanediol added. The carbopol was dissolved in water and mixed with the pentanediol solution, after which the viscosity was adjusted with an aqueous solution of NaOH.

This Example shows the Typical constituents for a composition in the form of a gel and additionally in which 1-glycerol monolaurate is used as the sole monoglyceride.

The effectiveness of the gel corresponds to the effectiveness of the cream in Example 2.

EXAMPLE 4

Fusidic acid in crystalline monoglycerides with an enhanced antimicrobial spectrum.

A composition with the following composition by weight was prepared:

| | |
|---|---|
| Fusidic acid | 2% |
| 1-glycerol monolaurate | 7% |
| 1-glycerol monomyristate | 21% |
| Purified water | to 100% |

During preparation, the monoglycerides were mixed with water and heating carried out to 70° C. The fusidic acid was then added, after which mixing was effected for 15 minutes at said temperature after which the resultant mixture was cooled at a rate of 1°–3° C. per minute to room temperature. Optional buffering of the pH and addition of thickening agents is done prior to cooling of the mixture.

An MIC value determination showed that the composition had a lower MIC value than a commercial preparation of fusidic acid and that the antimicrobial spectrum was enhanced with regard to effectiveness on fungi.

EXAMPLE 5

Antibacterial preparation containing econazole nitrate

A composition with the following composition by weight was prepared:

| | |
|---|---|
| Econazole nitrate | 1% |
| 1-glycerol monolaurate | 7% |
| 1-glycerol monomyristate | 21% |
| Purified water | to 100% |

The composition was prepared in the same manner as the composition of Example 4. Investigation of the antimicrobial properties of the composition showed it to have antimicrobial effectiveness in contrast to a commercial product containing only econazole nitrate in the same concentration as the above preparation.

EXAMPLE 6

Ache preparation containing tinidazole

A composition with the following composition by weight was prepared:

| | |
|---|---|
| Tinidazole | 2% |
| 1-glycerol monolaurate | 5% |
| 1-glycerol monomyristate | 15% |
| Propylene glycol | 30% |
| Carbomer | 0.5% |
| Purified water | to 100% |

The composition was prepared as in Example 4. It proved to have a powerful killing effect on fungi and bacteria, both aerobic and anaerobic, in contrast to aqueous solutions of tinidazole which are not effective against aerobic bacteria. In particular, the product is usable for disease states such as acne and seborrhoea.

EXAMPLE 7

Microbiologically stabilized preparation containing urea

The following composition was prepared:

| | |
|---|---|
| Urea | 10% |
| Phosphate buffer to pH 6.0 | q.s. |
| 1-glycerol monolaurate | 7% |
| 1-glycerol monomyristate | 21% |
| Purified water | to 100% |

The composition was prepared as in Example 4.

In microbiological load tests, it proved to have bacteriocidal and fungistatic properties. Both the bactericidal and fungistatic effects are more powerful than that provided by either the monoglycerides or urea individually.

Monolaurin can also be added to the emulsion in order to enhance the antimicrobial effectiveness, either in solution, in an aqueous phase, in crystalline form in an aqueous phase or dissolved in a lipid phase. It is important that crystalline monolaurin is added at a temperature below 35° C. in order to avoid effects on the formation of the emulsion. Smaller amounts of monolaurin can be added at the emulsifying temperature (around 70° C). Lipid or water soluble medicaments are then dissolved in the phase in which their solubility is highest. This is exemplified in Examples 8 and 9 below.

EXAMPLE 8

Emulsion containing urea

An emulsion of the water-in-oil type with the following composition was prepared:

| | |
|---|---|
| Liquid paraffin | 20 g |
| Monolaurin | 1 g |
| Sorbitan monooleate | 1 g |
| Water | 50 g |
| Polyoxyethylene (20) stearate | 1 g |
| Carbomer | 0.5 g |

Components 1, 2 and 3 were mixed and heated to 70° C. Separately, components 4, 5 and 6 were blended and heated to 70° C. The mixtures were homogenized and cooled to room temperature. After cooling, urea was added in an amount corresponding to 1–10 g in 26.5 g of water.

EXAMPLE 9

Emulsion containing monolaurin

An emulsion of the oil-in-water type was prepared from the following ingredients:

| | |
|---|---|
| A | |
| Liquid paraffin | 20 g |
| Sorbitan monooleate | 1 g |
| Water | 20 g |
| Polyoxyethylene (20) stearate | 1 g |
| Carbomer | 0.5 g |
| B | |
| Monolaurin | 5 g |
| Monomyristin | 15 g |
| Water | 37.5 g |

Emulsion A was prepared as earlier described and cooled to around 35° C. Lipid crystal dispersion B was prepared in the following manner. The components were mixed at 70° C. and after 15 minutes the mixture was cooled at a rate of 1°–3° per minute. When crystallisation was complete, A and B were mixed at 30°–35° C.

Over and above what has been said earlier regarding the components forming part of the composition, it should be added that the practice of the invention has shown that it does not matter in what form the monoglycerides are present. In other words, it has proven that the monoglyceride has the same or a similar potentiating effect on antimicrobial properties whether it is present in solution, in amorphous form or in crystalline form. In this respect also, the invention thereby represents a valuable contribution to the art.

We claim:

1. An antimicrobial composition, which comprises an antimicrobially effective amount of a combination of:
   A) a monoglyceride selected from the group consisting of a monoglyceride of lauric acid, a monoglyceride of myristic acid and a mixture of these monoglycerides, and
   B) at least one chemical substance selected from the group consisting of urea, fusidic acid, econazole nitrate, (1-(2,4-di-chloro-beta-(p-chlorobenzyloxy)-phenethyl)imidazol nitrate), mikonazole nitrate (1((2(2,4-di-chlorophenyl)-2((2,4-dichlorophenyl)methoxy)-ethyl)-1H-imidazol nitrate), tinidazole (1-(2-(ethylsulphonyl)ethyl)-2-methyl-5-nitroimidazole), metronidazole (1-(2-hydroxyethyl)- 2-methyl-5-nitroimidazole and pentanediol, and
   c) optionally, a conventional physiologically acceptable carrier and/or physiologically acceptable additives, the concentration of A) being from 0.2 ppm to 30% and of B) being from 1 ppm to 20%, in both cases calculated as weight of the total weight of the composition.

2. A composition according to claim 1, wherein the chemical substance B) is fusidic acid.

3. A composition according to claim 1, wherein the chemical substance B) is econazole nitrate.

4. A composition according to claim 1, wherein the chemical substance B) is tinidazole.

5. A composition according to claim 1, wherein the chemical substance B) is urea.

6. A composition according to claim 1, wherein the pentanediol is 1,5-pentanediol.

7. A composition according to claim 1, wherein the monoglyceride A) is a monolaurate.

8. A composition according to claim 1 which contains from 1 ppm to 20% of the chemical substance(s) B), calculated as weight on the total weight of the composition.

9. A process for the preparation of an antimicrobial composition as defined in claim 1 comprising heating the monoglyceride(s) A) to a temperature over the transition or conversion temperature of the lipid, optionally in the presence of a carrier and/or additives C), adding the substance(s) B) to the heated mixture until conversion has taken place, and cooling the substance(s) B-containing mixture to around room temperature.

10. A process according to claim 9, wherein the cooling is carried out at a rate of around 1°–3° C. per minute.

11. A composition according to claim 1 which is suitable for use as an antimicrobial pharmaceutical composition.

12. A method of using a composition as defined in claim 1 for combatting bacteria and/or fungi.

13. A method of using a composition as defined in claim 1 to stabilize a cosmetic product, a food product, or a medical product, comprising adding an amount of said composition to a cosmetic product, a food product or a medical product effective to enhance the stability thereof.

14. A composition according to claim 2, wherein the monoglyceride A) is a monolaurate.

15. A composition according to claim 3, wherein the monoglyceride A) is a monolaurate.

16. A composition according to claim 4, wherein the monoglyceride A) is a monolaurate.

17. A composition according to claim 5, wherein the monoglyceride A) is a monolaurate.

18. A composition according to claim 6, wherein the monoglyceride A) is a monolaurate.

19. A composition according to claim 2, which contains from 1 ppm to 20% of the chemical substance(s) B), calculated as weight on the total weight of the composition.

20. A composition according to claim 3, which contains from 1 ppm to 20% of the chemical substance(s) B), calculated as weight on the total weight of the composition.

21. The composition according to claim 7, where the monolaurate is 1-glycerol monolaurate or 3-glycerol monolaurate.

22. The composition according to claim 15, wherein the monolaurate is 1-glycerol monolaurate or 3-glycerol monolaurate.

23. The composition according to claim 16, wherein the monolaurate is 1-glycerol monolaurate or 3-glycerol monolaurate.

24. The composition according to claim 17, wherein the monolaurate is 1-glycerol monolaurate or 3-glycerol monolaurate.

25. The composition according to claim 18, wherein the monolaurate is 1-glycerol monolaurate or 3-glycerol monolaurate.

26. The composition of claim 8 wherein the amount of the chemical substance(s) B), calculated as weight on the total weight of the composition ranges from 0.1 to 10%.

27. The composition of claim 19 which contains from 0.1 to 10% of the chemical substance(s) B), calculated as weight on the total weight of the composition.

28. The composition of claim 20 which contains from 0.1 to 10% of the chemical substance(s) B), calculated as weight on the total weight of the composition.

* * * * *